Figure 1:
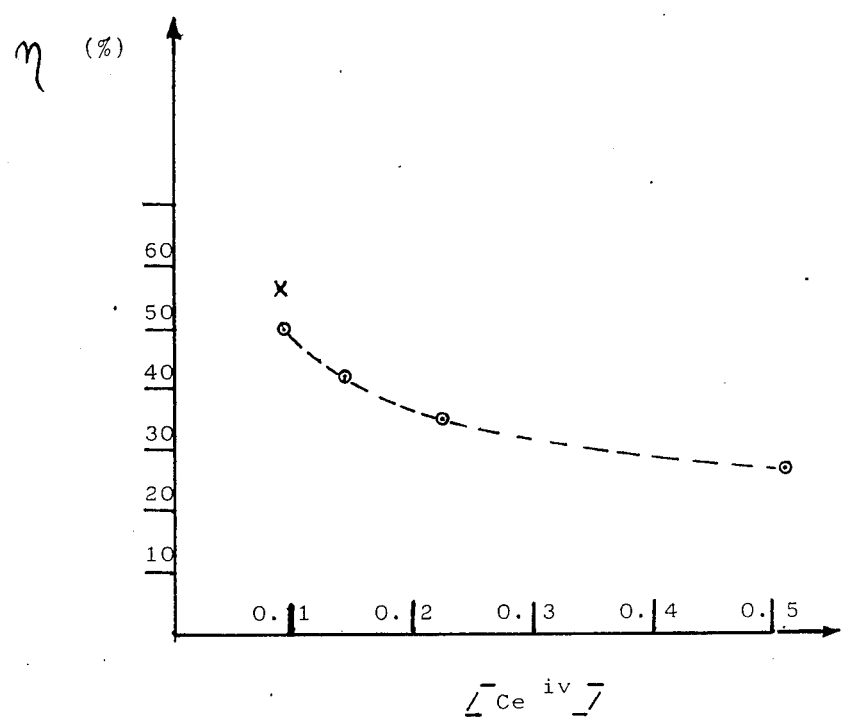

United States Patent [19]

Foa' et al.

[11] Patent Number: 4,689,433
[45] Date of Patent: Aug. 25, 1987

[54] PROCESS FOR THE MANUFACTURE OF O-NITROBENZALDEHYDE

[75] Inventors: Marco Foa', Novara; Norberto Gatti, Galliate, both of Italy

[73] Assignee: Montedison S.p.A., Milan, Italy

[21] Appl. No.: 872,484

[22] Filed: Jun. 10, 1986

[30] Foreign Application Priority Data

Jun. 13, 1985 [IT] Italy ................. 21136 A/85

[51] Int. Cl.$^4$ ............................................. C07C 79/36
[52] U.S. Cl. ......................................................... 568/424
[58] Field of Search ....................................... 568/424

[56] References Cited

PUBLICATIONS

Syper, Tetrahedron Letters, No. 37 (1966), 4493-4498.

Primary Examiner—Werren B. Lone
Attorney, Agent, or Firm—Stevens, Davis, Miller & Mosher

[57] ABSTRACT

A process for the manufacture of o-nitrobenzaldehyde by oxidation of o-nitrotoluene, characterized in that o-nitrotoluene is made to react with an aqueous solution containing Cerium$^{iv}$ perchlorate and from 5 to 9 moles/liter of perchloric acid; according to a preferred embodiment, the dispersion of o-nitrotoluene in an aqueous solution containing from 5 to 9 moles per liter of perchloric acid is first prepared and then an aqueous solution is gradually added, containing Cerium$^{iv}$ perchlorate and 5-9 moles/liter of perchloric acid.

5 Claims, 1 Drawing Figure

○ Toluene - 2.3 times the stoichiometrical
× Toluene - 9.0 times the stoichiometrical

PROCESS FOR THE MANUFACTURE OF O-NITROBENZALDEHYDE

The invention concerns a process for the manufacture of o-nitrobenzaldehyde by oxidation of o-nitrotoluene; besides representing a useful intermediate in organic synthesis, o-nitrobenzaldehyde is the main raw material for the preparation of nifedipine, which is a known drug.

BACKGROUND OF THE INVENTION

It is known to prepare o-nitrobenzaldehyde starting from o-nitrotoluene and from an alkyl-oxalate, in the presence of an alcoholate, thereby obtaining o-nitrophenylpyrruvic acid, which is then oxidized with sodium hypochlorite, in order to get the corresponding benzal chloride, subsequently hydrolized to the corresponding aldehyde; such process is quite burdensome because of the necessity of using a three-step reaction and of the presence of an alcoholate. A photochemical bromination of o-nitrotoluene to the corresponding benzal bromide and subsequent alkaline hydrolysis of the bromide were also described, but this method proved to be of very little practical interest because benzal bromide can explode and because of the non-selectivity of the bromination reaction.

One object of the invention is that of providing a simple and cheap process for the preparation of o-nitrobenzaldehyde by oxidation of o-nitrotoluene with an oxidizing agent which can easily be regenerated at the end of the reaction and which may then be repeatedly re-used. Another object is that of providing a process ensuring a very good selectivity to o-nitrobenzaldehyde and satisfactory yields with respect to the oxidizing agent. A still further object is that of providing a process that can be carried out under mild temperature conditions, within short operational times and as a continuous cycle.

DISCLOSURE OF THE INVENTION

The objects hereinabove and still other objects can be easily reached by a process characterized in that o-nitrotoluene is made to react with an aqueous solution containing Cerium$^{iv}$ perchlorate and from 5 to 9 moles/liter of perchloric acid, the reaction being the following:

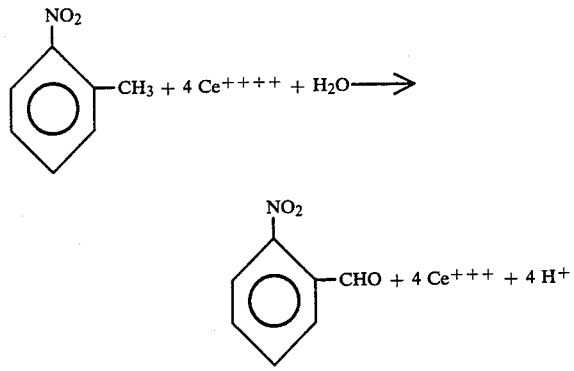

o-nitrotoluene and Ce++++ may be used stoichiometric amounts (that is, 1 mole of o-nitrotoluene/4 mols of Ce$^{iv}$).

It is however preferable to use o-nitrotoluene in amounts from 1.8 to 20 times greater than the stoichiometric requirement, i.e. it is better to use from 0.45 to 5 moles of o-nitrotoluene per mole of Ce$^{iv}$.

According to a preferred embodiment, one may prepare an o-nitrotoluene dispersion within an aqueous solution of 5-9N perchloric acid and then add to such a dispersion the aqueous solution of Ce$^{iv}$ perchlorate and 5-9N perchloric acid, all just in one single run.

It is however preferable to gradually add the aqueous solution of Ce$^{iv}$ perchlorate and perchloric acid to the dispersion, so as to limit the steady concentration of Ce$^{iv}$ in the reaction mixture; this latter procedure ensures a better yield with respect to Ce$^{iv}$.

When the aqueous solution of Ce$^{iv}$ perchlorate and perchloric acid is gradually added to the dispersion hereinabove, the Ce concentration of such a solution, in general, is between 0.05 and 0.6 moles/liter; the concentration of the perchloric acid in the aqueous solution should be, as already explained, between 5 and 9 but preferably between 6 and 8 moles/liter. The reaction, in general, should be performed at 50°-90° C. and preferably at 60°-80° C. Before the first reaction step, it is suitable to prepare an aqueous solution of Ce perchlorate and perchloric acid, and to electrolyze this solution in order to convert part of the Ce$^{iii}$ into Ce$^{iv}$; the thus obtained oxidizing solution is then used in the first reaction step and at the end of the oxidation the spent solution is regenerated by electrolysis, in order to restore the required amount of Ce$^{iv}$. One may carry out repeated alternating stages of o-nitrotoluene oxidation and electrolytic regeneration of the oxidizing agent without meeting any sort of drawbacks or shortcomings.

The starting aqueous solution of Ce$^{iii}$ perchlorate and perchloric acid may be prepared by dissolving carbonate, oxalate or oxide of Ce$^{iii}$ in aqueous perchloric acid, until obtaining, for instance, a solution containing from 0.07 to 1 moles of Ce$^{iii}$/liter; successively an electric current is made to pass through the solution. The ions introduced during the preparation of the Ce$^{iii}$ perchlorate and perchloric acid solution, disappear inasmuch as the carbonate decomposes whithin the acid medium, thereby developping $CO_2$, while the oxalate is oxidized to $CO_2$ during the electrolysis. The electrolytical cell for the oxidation of part of the Ce$^{iii}$ to Ce$^{iv}$ and for the regeneration of the exhausted oxidizing solution, is characterized by known features and also works in a known way; the cell may lack compartments or may own anodic and cathodic compartments separated from each other by a membrane or by a porous diaphragm The electrodes may consist of any kind of corrosion-resistant electrodic meterial; the anode may consist in particular of Pt or $PbO_2$; the cathode of Pt, Cu, stainless steel and graphite. The current density is not a critical parameter and is determined as a function of the size of the electrolytical cell, of the desired electrochemical reaction time and of the addition rate of the Ce$^{iv}$ solution to the reaction medium. The electrolytical oxidation, in general, should be performed at 10° C.-30° C. under mechanical, stirring; should one operate in a continuous cycle, however, the movement of the solution in the cell, and the turbulence generated by the gases ($H_2$ and $O_2$) that form during the electrochemical reaction, can supply a sufficient stirring. As already explained, it is preferable to gradually add the aqueous solution of Ce$^{iv}$ perchlorate and perchloric acid to the reaction medium, thus obtaining a suspension of o-nitrotoluene in an aqueous solution of Ce$^{iii}$ and 5-9N perchloric acid. Because of the insolubilty of the organic substance in the aqueous solution, the suspension must be vigorously stirred, for instance by means of a VIBROMIXER; still under stirring, the suspension is then gradually additioned with the solution of $Ce^{iv}$ in aqueous 5–9N perchloric acid. When an excess of o-nitrotoluene is (preferably) used, the end of the reaction is provided by the disappearance of the typical colour of the $Ce^{iv}$ ion. The organic products are then separated from the acid-aqueous mixture by means of any usual technique, for instance by extraction with an organic solvent such as ethyl ether, $CH_2Cl_2$ or $CHCl_3$. The o-nitrobenzaldehyde can be separated from o-nitrotoluene by means of any usual technique, for instance by extraction with an aqueous solution of sodium bisulphite; the aldehyde-bisulphite adduct is subjected to either alkaline or acid hydrolysis, and the o-nitrobenzaldehyde is recovered by extraction with a solvent, for instance ethyl ether, $CH_2Cl_2$ or $CHCl_3$. The o-nitrotoluene, separated from the aldehyde, is then recycled back to the reaction stage. The process according to the invention may be carried out in a continuous cycle and its main advantages may be thus summarized:

the process is simple and cheap, ensures a very good selectivity to o-nitrobenzaldehyde and gives satisfactory yields with respect to $Ce^{iv}$;

the oxidation step may be performed under mild temperature conditions and within short times, the oxidizing agent being easily and repeatedly regenerated in an electrolytical cell;

the process may be carried out as a continuous cycle.

The following examples are given in order to illustrate the invention, without any limitation, however, of the scope thereof.

EXAMPLE 1

25 g of $Ce_2(CO_3)_3 \cdot H_2O$ were dissolved in 300 cm$^3$ of an aqueous solution of 7,8N $HClO_4$. Thereafter 250 cm$^3$ of the thus obtained solution were electrolyzed in a 400 cm$^3$ electrolytical cell, under a constant current of 500 mA.

The Pt-anode had a surface of about 20 cm$^2$ and the Cu-cathode had a surface of about 1 cm$^2$. The whole electrical load was 3650 coulomb. The resulting 0.069M solution of $Ce^{iv}$ was 6,7N with respect to $HClO_4$. Into a 500 cm$^3$ reactor, fitted with Vibromix stirrer, reflux condenser, dripping funnel and thermometer, were introduced, under nitrogen atmosphere, 6.0 g of o-nitrotoluene (43.9 mmoles) and 50 cm$^3$ of an aqueous solution of $Ce^{iii}$ perchlorate and 6,7N perchloric acid (that is the $Ce^{iii}$ solution previously prepared but not electrolyzed). The mixture was heated up to 70° C. and then gradually additioned, at a constant rate of 1.5 cm$^3$/minute, with 230 cm$^3$ of the $Ce^{iv}$ solution (15.9 mmoles) in perchloric acid obtained after the electrolytical treatment; the amount of o-nitrotoluene was 11 times greater than the stoichiometric requirement. At the end of the dripping, the reaction mass was brought down to room temperature, extracted with $CH_2Cl_2$ and then anhydrified on $Na_2SO_4$. The gaschromatographic analysis (with an internal phenylbenzoate standard) showed the presence of 0.325 g of o-nitrobenzaldehyde; the aldehyde yield, with respect to $Ce^{iv}$ was 54%.

EXAMPLE 2

Into the reactor of example 1, were introduced, under nitrogen atmosphere, 5.6 g of o-nitrotoluene (41.2 mmoles) and 60 cm$^3$ of 7,8N $HClO_4$; the mixture was heated up to 70° C. and then gradually additionated, at a constant rate of 1.5 cm$^3$/minute, with 228 cm$^3$ of a 0.08M solution of $Ce^{iv}$ (18.2 mmoles) in 7,5N $HClO_4$. The amount of o-nitrotoluene was 9 times greater than the stoichiometric requirement. At the end of the dripping, the reaction mass was cooled down to room temperature, then extracted with $CH_2Cl_2$ and dehydrated on $Na_2SO_4$. The gaschromatographic analysis showed the presence of 0.45 g of o-nitrobenzaldehyde, corresponding to a 66% yield with respect to $Ce^{iv}$.

EXAMPLE 3

Into the reactor of example 1 were introduced, under nitrogen atmosphere, 1.8 g of o-nitrotoluene (13.0 mmoles) and 60 cm$^3$ of 7,8N $HClO_4$; the mixture was heated up to 70° C. and then gradually additioned, at a constant rate of 1.5 cm$^3$/minute, with 45 cm$^3$ of a 0.51M solution of $Ce^{iv}$ (22.8 mmoles) in 7,3N $HClO_4$. The amount of o-nitrotoluene was 2.3 times greater than the stoichiometric requirement. At the end of the dripping, it was proceeded as in ex. 1, thereby obtaining 0.234 g of o-nitrobenzaldehyde, corresponding to a 27% yield with respect to $Ce^{iv}$. The run was then repeated three other times, lowering the $Ce^{iv}$ molar concentration down respectively to:

0.22 moles/liter
0.14 moles/liter
0.09 moles/liter keeping always the amount of $Ce^{iv}$ at the same level (22.8 millimoles); the better yields are recorded on FIG. 1, together with the yield of a test in which the toluene amount was 9 times the stoichiometrical need.

EXAMPLE 4

Into the reactor of example 1 were introduced, under nitrogen atmosphere, 1.5 g of o-nitrotoluene (11.3 mmoles) and 60 cm$^3$ of 7,8N $HClO_4$; the mixture was heated up to 70° C. and then gradually additioned, at a constant rate of 1.5 cm$^3$/minute, with 245 cm$^3$ of a 0.093M solution of $Ce^{iv}$ (22.8 mmoles) in 7,7N $HClO_4$. The amount of o-nitrotoluene was 1.98 times greater than the stoichiometric requirement. At the end of the dripping, it was proceeded in the same way as in example 1, thereby obtaining 0.43 g of o-nitrobenzaldehyde corresponding to a 50% yield with respect to $Ce^{iv}$.

EXAMPLE 5

Into the reactor of example 1 were introduced, under nitrogen atmosphere, 6.5 g of o-nitrotoluene (47.4 mmoles) and 50 cm$^3$ of a 0.71M aqueous solution of $Ce^{iii}$ (5.7N in $HClO_4$). The mixture was heated up to 70° C. and then gradually additioned, at a constant rate of 1.5 cm$^3$/minute, with 218 cm$^3$ of a 0.60M solution of $Ce^{iv}$ (13.1 mmoles) in 5.7N $HClO_4$. The amount of o-nitrotoluene was 14.5 times greater than the stoichiometric requirement. At the end of the dripping, it was proceeded as in example 1, obtaining 0.17 g of o-nitrobenzaldehyde, namely a 34.4% yield with respect to $Ce^{iv}$.

EXAMPLE 6

Into the reactor of example 1 were introduced under nitrogen atmosphere, 9.96 g of o-nitrotoluene (72.7 mmoles) and 60 cm$^3$ of 7,8N $HClO_4$; the mixture was heated up to 70° C. and then gradually additioned, at a constant rate of 1.5 cm$^3$/minute, with 220 cm$^3$ of a 0.081M solution of $Ce^{iv}$ (17.9 mmoles) in 7,7N $HClO_4$. The amount of o-nitrotoluene was 16.2 times greater than the stoichiometric requirement. At the end of the dripping, it was proceeded like in example 1 obtaining 0.42 g of o-nitrobenzaldehyde, namely a 62% yield with respect to $Ce^{iv}$.

EXAMPLE 7

Into the reactor of example 1 were introduced, under nitrogen atmosphere, 4.46 g of o-nitrotoluene (32.5 mmoles) and 60 cm$^3$ of 7,8N HClO$_4$; the mixture was heated up to 70° C. and then gradually additioned, at a constant rate of 30 cm$^3$/minute, with 220 cm$^3$ of a 0.081M solution of $Ce^{iv}$ (17.9 mmoles) in 7,7N HClO$_4$. The amount of o-nitrotoluene was 7.2 times greater than the stoichiometric requirement. At the end of the dripping it was proceeded as in example 1, obtaining 0.34 g of o-nitrobenzaldehyde, namely a 50% yield with respect to $Ce^{iv}$.

What we claim is:

1. A process for the manufacture of o-nitrobenzaldehyde, by oxidation of o-nitrotoluene, characterized in that an aqueous solution consisting essentially of aqueous cerium$^{iv}$ perchlorate containing from 0.05 to 0.60 moles/liter of $Ce^{iv}$ and from 5 to 9 moles/liter of aqueous perchloric acid is gradually added to a dispersion of o-nitrotoluene in an aqueous solution consisting essentially of from 5 to 9 moles/liter of aqueous perchloric acid, said dispersion being at 50°–90° C.

2. A process according to claim 1, wherein the amount of o-nitrotoluene is from 1.8 to 20 times greater than the stoichiometrical requirement.

3. A process according to claim 1, wherein the HClO$_4$ concentration in said aqueous solution is from 6 to 8 moles/liter.

4. A process according to claim 1, wherein the said dispersion is at 60°–80° C.

5. A process for the manufacture of o-nitrobenzaldehyde, by oxidation of o-nitrotoluene, characterized in that an aqueous solution consisting essentially of aqueous cerium$^{iv}$ perchlorate containing from 0.05 to 0.60 moles/liter of $Ce^{iv}$ and from 5 to 9 moles/liter of aqueous perchloric acid, wherein the cerium$^{iv}$ perchlorate is obtained by electrochemical oxidation of $Ce^{iii}$ carbonate or $Ce^{iii}$ oxalate in the presence of aqueous perchloric acid, is gradually added to a dispersion of o-nitrotoluene in an aqueous solution consisting essentially of from 5 to 9 moles/liter of aqueous perchloric acid, said dispersion being at 50°–90° C.

* * * * *